(12) United States Patent
Ripka

(10) Patent No.: US 9,675,724 B1
(45) Date of Patent: Jun. 13, 2017

(54) SCENT DISPENSER SYSTEM AND METHOD OF DISPENSING SCENT FROM A LIQUID

(71) Applicant: Lee Winfield Ripka, Rebersburg, PA (US)

(72) Inventor: Lee Winfield Ripka, Rebersburg, PA (US)

( * ) Notice: Subject to any disclaimer, the term of this patent is extended or adjusted under 35 U.S.C. 154(b) by 0 days.

(21) Appl. No.: 14/816,493

(22) Filed: Aug. 3, 2015

Related U.S. Application Data

(62) Division of application No. 13/426,675, filed on Mar. 22, 2012, now Pat. No. 9,125,396.

(60) Provisional application No. 61/466,336, filed on Mar. 22, 2011.

(51) Int. Cl.
 *A61L 9/12* (2006.01)
 *A01M 31/00* (2006.01)
 *A01M 1/20* (2006.01)

(52) U.S. Cl.
 CPC ............ *A61L 9/12* (2013.01); *A01M 1/2055* (2013.01); *A01M 31/008* (2013.01)

(58) Field of Classification Search
 CPC ...... A01M 31/008; A01M 1/2055; A61L 9/12
 USPC ........... 239/6, 34, 54, 55, 60, 128, 135–139; 119/711
 See application file for complete search history.

(56) References Cited

U.S. PATENT DOCUMENTS

| | | | | |
|---|---|---|---|---|
| 2,738,224 A | * | 3/1956 | Checkovich | A61L 9/12 239/57 |
| 2,763,395 A | * | 9/1956 | Meek | B05B 11/00 220/23.89 |
| 3,046,192 A | * | 7/1962 | Bilyen | A01M 31/00 239/56 |
| 4,063,665 A | * | 12/1977 | Schneider | B65D 83/00 222/129 |
| 4,165,835 A | * | 8/1979 | Dearling | A61L 9/12 239/45 |
| 4,286,754 A | * | 9/1981 | Jones | A61L 9/127 239/44 |
| 4,346,840 A | * | 8/1982 | Gaiser | A61L 9/04 239/54 |
| 5,746,019 A | * | 5/1998 | Fisher | A01M 31/008 239/145 |
| 6,089,947 A | * | 7/2000 | Green | A61L 9/12 119/711 |
| 6,213,409 B1 | * | 4/2001 | Warren | A61L 9/042 239/34 |
| 6,749,479 B2 | * | 6/2004 | Vick | A61L 9/12 446/369 |
| 7,138,367 B2 | * | 11/2006 | Hurry | A01N 25/04 239/34 |
| 7,528,102 B2 | * | 5/2009 | Barthel | A47L 15/4445 422/5 |

\* cited by examiner

*Primary Examiner* — Arthur O Hall
*Assistant Examiner* — Alexander Valvis
(74) *Attorney, Agent, or Firm* — John J. Elnitski, Jr.

(57) ABSTRACT

A scent dispenser system used for dispensing scent from a liquid. The system includes a dispenser having an open volume. The system includes absorbent beads in the open volume of the dispenser, where the absorbent beads having the capability to absorb a liquid. The system includes aeration windows in the dispenser to receive a liquid and to allow air to pass through the dispenser and about the absorbent beads.

1 Claim, 9 Drawing Sheets

SCENT DISPENSER SYSTEM AND METHOD OF DISPENSING SCENT FROM A LIQUID

This application is a divisional of U.S. application Ser. No. 13/426,675 and claims the benefit of and incorporates by reference U.S. application Ser. No. 13/426,675 and U.S. Provisional Application No. 61/466,336 filed Mar. 22, 2011.

BACKGROUND

The present invention relates generally to dispensers of scents, and more particularly to animal lure scent dispensers used by hunters.

There are different scent dispensers of scents on the market. They are commonly used in the auto markets, home markets and hunting markets. The auto markets and home markets use the scent dispensers to masks odors in automobiles and homes. The hunting markets use scent dispensers to lure animals to the location of the scent dispenser. There are several different types of scent dispensers. Some use a scent impregnated on fabric or paper. Others are sophisticated enough to spray or drop fluid at timed intervals.

The three main types of dispensers for hunting include mechanical, non-mechanical, and gravity fed. Mechanical scent dispensers require a liquid scent reservoir to function properly in conjunction with the dispensing unit. Mechanical scent dispensers only distribute the scent with preset times set by the user. Non-mechanical scent dispensers do not contain a reservoir of scent and therefore they lack the ability to contain high volumes of scent. Gravity fed scent dispensers require a liquid scent reservoir to function properly in conjunction with the dispensing unit. Gravity fed scent dispensers only distribute scent with preset times set by the user, and when barometric pressure changes. The common type of dispenser used in hunting employs a fabric wick that draws liquid scent from a reservoir. The fabric wick is held in a container that allows air to pass over the fabric wick and carry the scent. One of the issues with using scents with scent dispensers is the handling of the scents. The handling of the scent can be accidently transferred to the user and then the user undesirably smells of the scent, especially when the scent is in a liquid form.

An object of the present is to provide a scent dispenser system that is simplistic to use.

Another objection of the present invention is to provide a scent dispenser system that aids in preventing spilling of liquid scent on the user.

SUMMARY OF THE INVENTION

A scent dispenser system used for dispensing scent from a liquid. The system includes a dispenser having an open volume. The system includes absorbent beads in the open volume of the dispenser, where the absorbent beads having the capability to absorb a liquid. The system includes aeration windows in the dispenser to receive a liquid and to allow air to pass through the dispenser and about the absorbent beads.

DETAILED DESCRIPTION

The present invention is a scent dispenser system. The present invention eliminates the need for a liquid reservoir, and mechanical components to distribute scent. The present invention allows the user to distribute scent all the time. The present invention allows the user to distribute high volumes of scent without the need for a reservoir or the use of a wick type scent dispenser. The scent dispenser system includes a container 10 as shown in FIGS. 1-4, 6-9 and a scent dispenser 12 shown in FIGS. 4-9.

Figure 1:
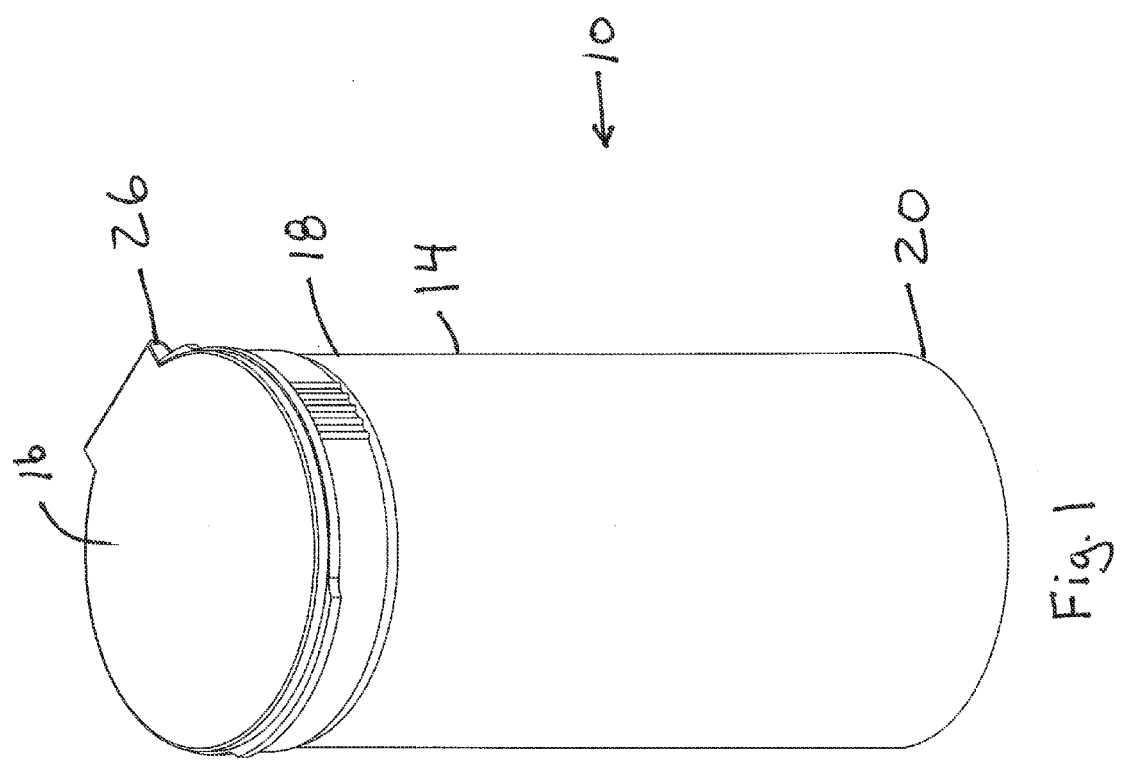
FIG. 1 is a perspective view of a container according to the present invention.
Figure 2:
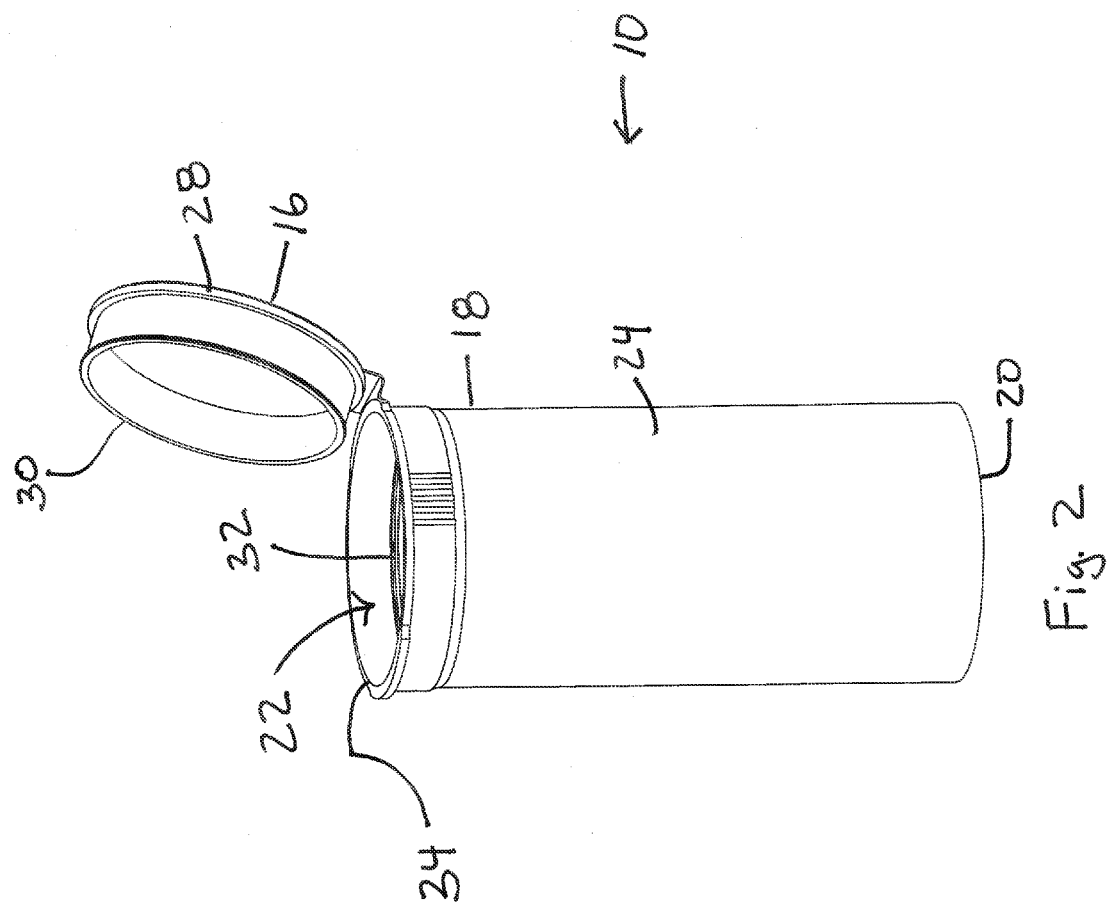
FIG. 2 is a perspective view of a container according to the present invention.
Figure 3:
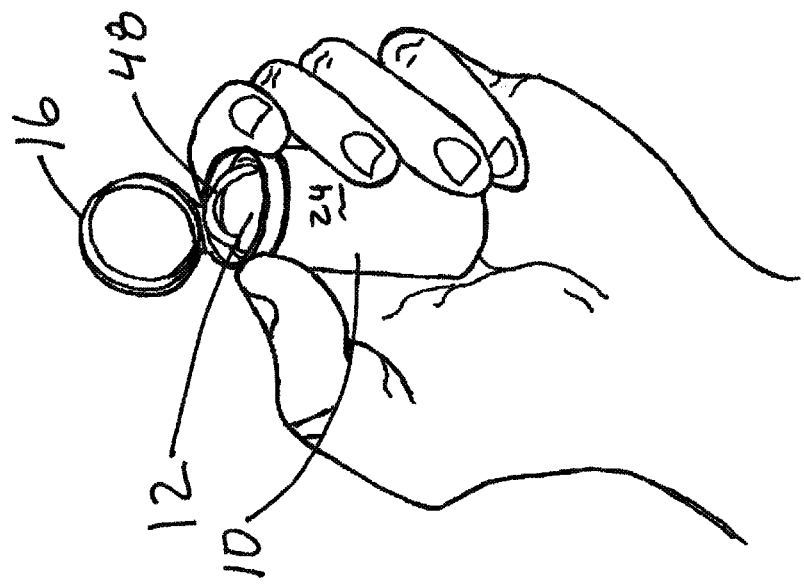
FIG. 3 is a perspective view of a container according to the present invention.
Figure 4:
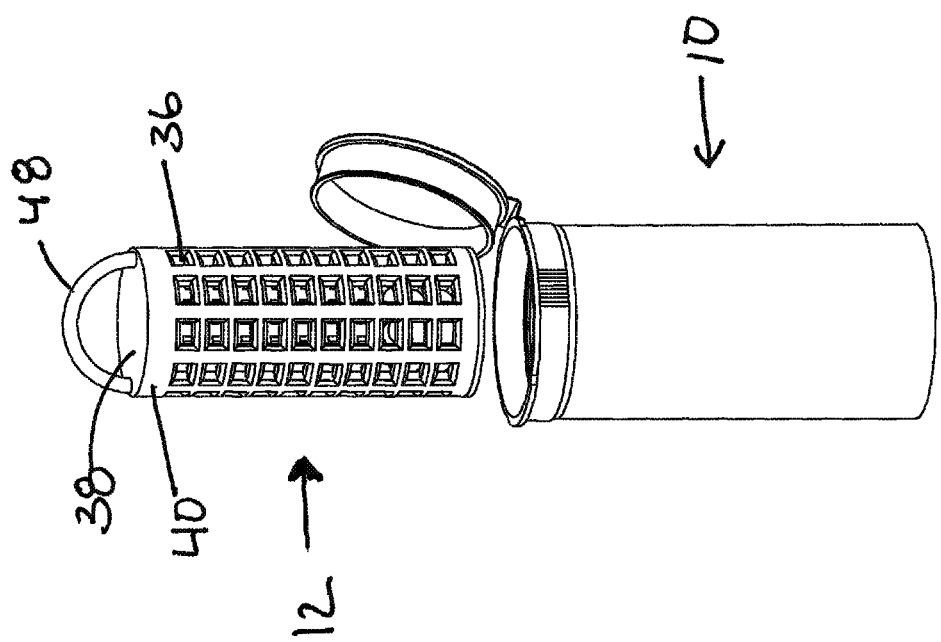
FIG. 4 is a perspective view of a container and dispenser according to the present invention.

The container 10 includes a main body 14 and a snap lid 16. The main body 14 and snap lid 16 can be made of polypropylene. The main body 14 has a top 18 and a bottom 20. The top 18 of the main body 14 has an opening 22 into the main body 14. The bottom 20 of the main body 14 is a solid piece of material that is attached to a wall 24 that forms the main body 14. The bottom 20 is connected to the wall 24 such to form a cylindrical container that can hold a liquid poured through the opening 22 of the top 18 of the main body 14. The snap lid 16 is connected to the top 18 by a flexible hinge 26. The snap lid 16 includes a top seal lip 28 and a bottom seal lip 30. The bottom seal lip 30 snaps into an internal groove 32 inside of the wall 24 of the main body 14 near the opening 22 at the top 18. The top seal lip 28 contacts the top 34 of the wall 24 about the opening 22 of the main body 14. When the snap lid 16 is pressed into the opening 22 of the main body 14, the bottom seal lip 30 snaps into the internal groove 32 and the top seal lip 28 is pressured against the top 34 of the wall 24. When the bottom seal lip 30 engages the internal groove 32 and pressures the top seal lip 28 against the top 34 of the wall 24, the container 10 is sealed in an air tight condition. The sealed container 10 can hold a liquid without the liquid leaking from the container 10, no matter what the orientation of the container 10 to gravity. Therefore, the container 10 can be placed in a user's pocket without fear of the liquid scent leaking from the container 10. FIG. 3 shows that to open the snap lid 16, the snap lid 16 is popped open by pressing on with two fingers on opposite sides of the wall 24 near the top 18. This acts as a safety feature to aid in preventing accidental opening of the snap lid 16.

Figure 5:
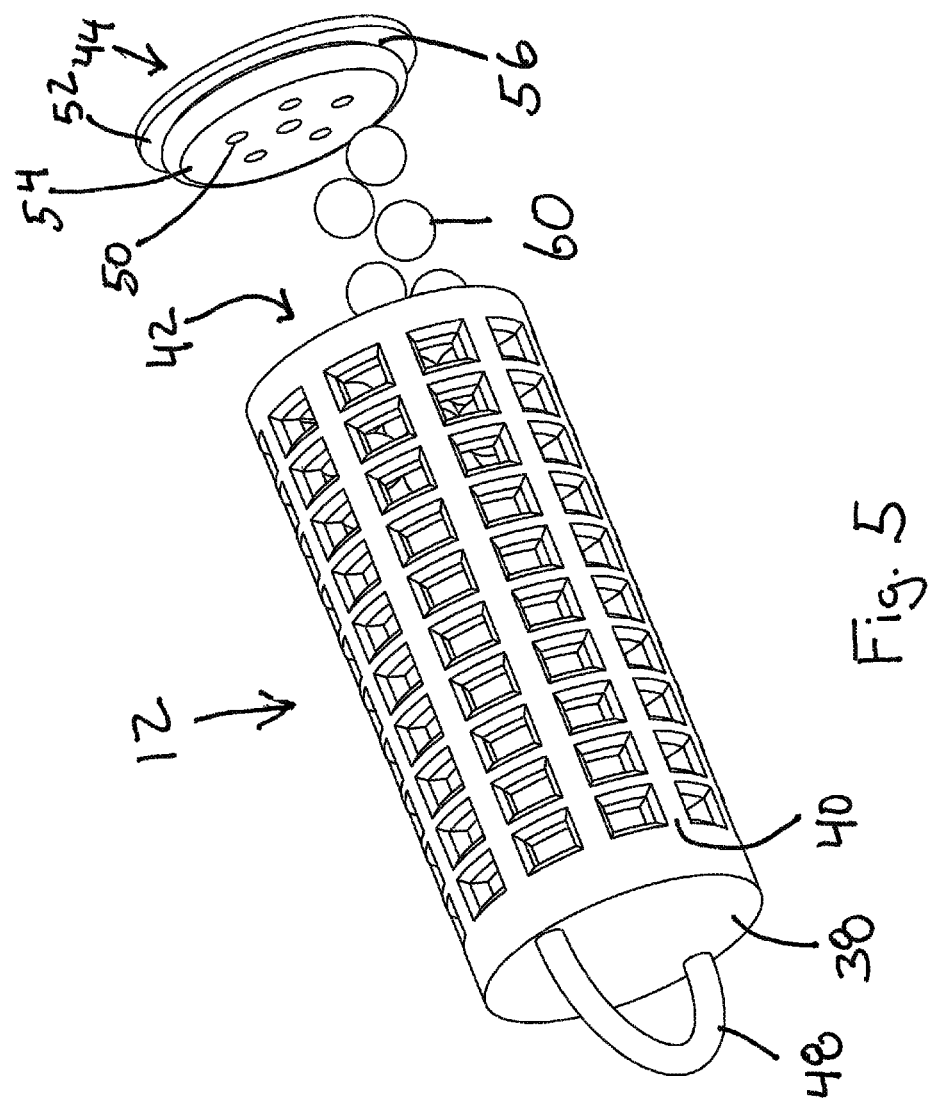
FIG. 5 is a perspective view of a dispenser according to the present invention.
Figure 6:
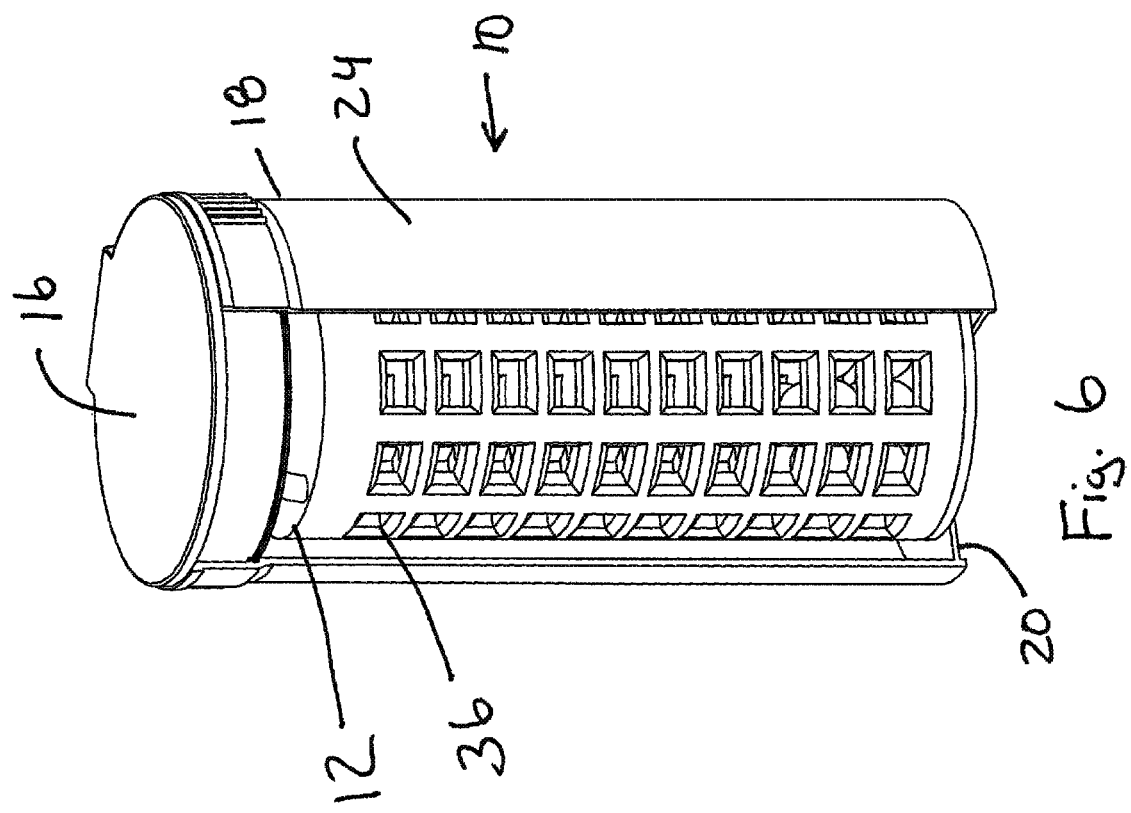
FIG. 6 is a cutaway view of a container and a perspective view of a dispenser according to the present invention.
Figure 7:
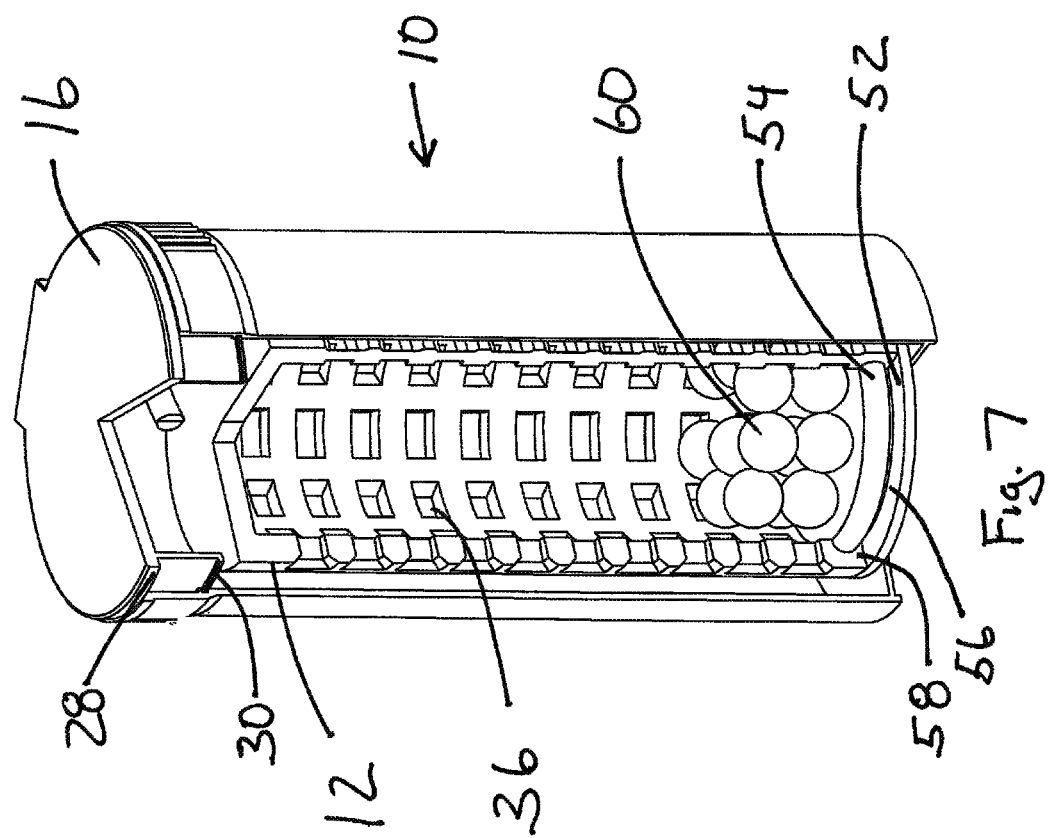
FIG. 7 is a cutaway view of a container and a dispenser according to the present invention.

The scent dispenser 12 is cylindrical container with aeration windows 36. The scent dispenser 12 can be of a molded silicone rubber. The scent dispenser includes a top 38, cylindrical wall 40, open bottom 42 and bottom cap 44. The top 38, cylindrical wall 40, open bottom 42 and bottom cap 44 of the scent dispenser 12 together form an open volume 46 with the top 38, cylindrical wall 40, open bottom 42 and bottom cap 44. The top 38 includes a flexible strap 48 to hang the dispenser 12. The cylindrical wall 40 includes the aeration windows 36. The bottom cap 44 includes aeration holes 50. The bottom cap 44 includes cap lip 52, plug 54 and groove 56 between the cap lip 52 and plug 54, as shown in FIG. 5. The scent dispenser 12 includes a locking lip 58 inside the cylindrical wall 40 along the open bottom 42, as shown in FIG. 5. The locking lip 58 engages the groove 56 between the cap lip 52 and plug 54, when the plug 54 is pressed into the open bottom 42 to hold the bottom cap 44 in place.

Figure 8:
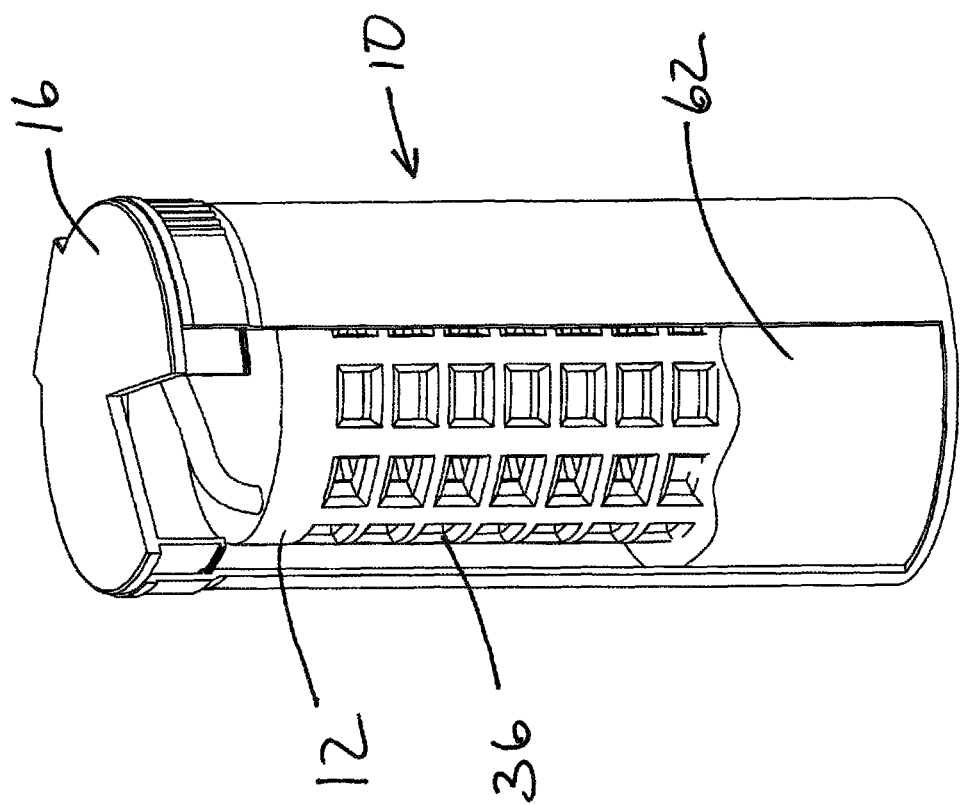
FIG. 8 is a cutaway view of a container and a perspective view of a dispenser according to the present invention.
Figure 9:
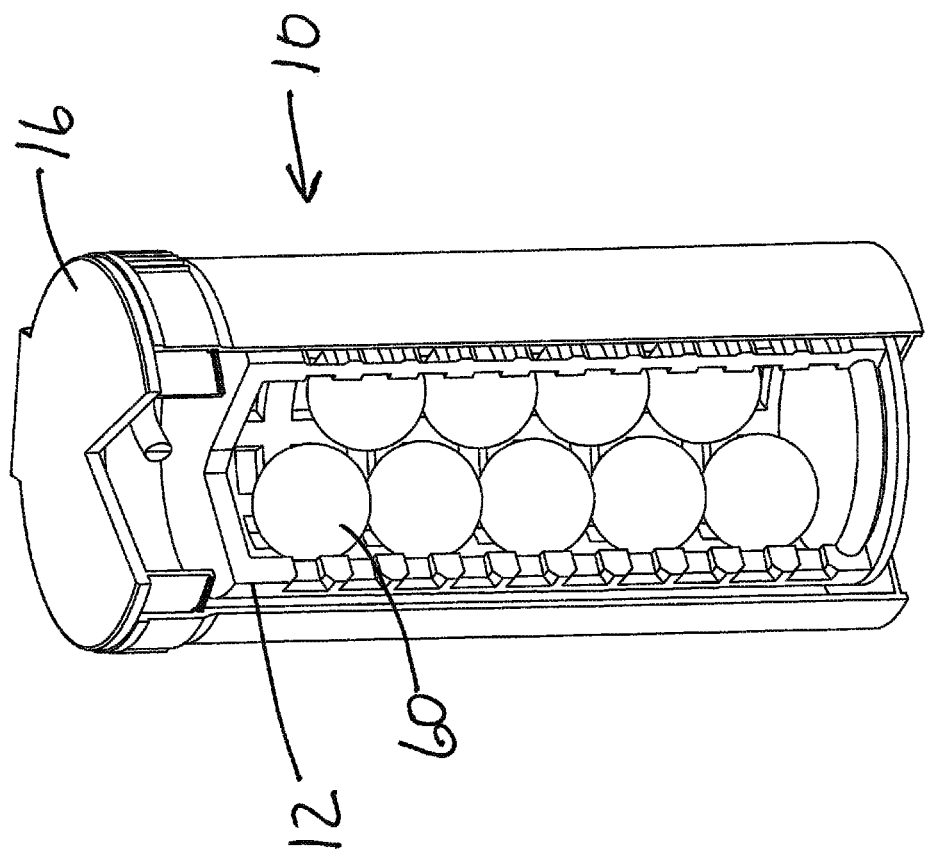
FIG. 9 is a cutaway view of a container and a dispenser according to the present invention.

FIGS. 6-9 show the scent dispenser 12 loaded into the container 10. FIGS. 5 and 7-9 show super absorbent beads 60 loaded in the open volume 46 of the scent dispenser 12. The absorbent beads 60 absorb liquid scent and hold the liquid scent for long periods of time. Examples of absorbent beads 60 are polymer crystals made from Polyacrylamide. The polymer crystals are good choice, as they have one of the highest capacities of absorption. For the present invention, the polymer crystals where formed into a 3-4 mm in size. The scent of the liquid scent is also absorbed by the absorbent beads 60. FIG. 8 shows liquid scent 62 in the container 10 with the scent dispenser 12. When the absorbent beads 60 shown in FIG. 7 come in contact with the liquid scent 62 shown in FIG. 8, the absorbent beads 60 absorb the liquid scent 62. The liquid scent 62 reaches the absorbent beads 60 by entering the aeration holes 50 in the bottom cap 44 and the aeration windows 36 of the wall 40. FIG. 9 shows the absorbent beads 60 after they have absorbed the liquid scent 62 and inflated in size within the open volume 46 in order to hold the liquid scent 62. If the right amount of liquid scent 62 is used, there will be no excess in the container 10 after hydration of the absorbent beads 60.

To hydrate the absorbent beads 60 using the liquid scent 62, the absorbent beads 60 can remain in contact with liquid scent 62 for as little as 1 second up to 1 hour. Polymer crystals used as the absorbent beads 60 can absorb thirty grams of liquid for every one gram of dry polymer crystal. The polymer crystals in the scent dispenser 12 absorbs more liquid scent 62 than any other non mechanical scent dispenser on the market, which allows the scent dispenser 12 to dispense scent for longer periods of time. There is approximately 2 grams of the 3-4 mm polymer crystals in the scent dispenser 12 having an open volume 46 of 0.95856 cubic inches. So, there should be roughly 2 grams of the 3-4 mm polymer crystals per every cubic inch in open volume 46 of the scent dispenser 12. If there is any more than 2 grams per cubic inch, the scent dispenser 12 could be overloaded and each polymer crystal could not be hydrated to its maximum. If there is less than 2 grams per cubic inch, the open volume 46 of the scent dispenser 12 will not be maximized when the polymer crystals are hydrated.

It was found that when using commercially available liquid scent to attract deer, the polymer crystal needed 30 minutes to properly absorb a water based liquid deer scent and up to an hour for an oil based liquid deer scent. The scent of the liquid scent is released through evaporation of liquid from absorbent beads 60 when air passes over the absorbent beads 60 through the aeration windows 36. This release of the scent through evaporation is over time. The release of the scent from the absorbed deer scent, can last from 10 to 20 days before the polymer crystals dry out. The scent dispenser 12 can be stored in the container 10 for up to 90 days with the liquid scent in the polymer crystals. The scent dispenser 12 has a perforated tube like structure to maximize air flow across the absorbent beads 60. The hydrated absorbent beads 60 stack on each other in the scent dispenser 12 such that there are air gaps between the absorbent beads 60. The air gaps between the absorbent beads 60 allow the air flowing through the scent dispenser 12 to flow between the absorbent beads 60 and carry away the scent using the evaporation process.

The method of the scent dispenser system start with opening the container 10 and pouring the liquid scent 62 into the container 10. Then, the scent dispenser 12 is placed into the container 10 to allow the absorbent beads 60 to absorb liquid scent 62. Time to fully absorb the liquid scent 62 depends on the absorbent bead material and the ingredient characteristics of the liquid scent. The scent dispenser 12 can then be removed from the container 10 and hung by the strap 48 to allow the scent to be distributed. An example would be to hang the scent dispenser 12 on tree limb or rear view mirror. The scent dispenser system could be sold with the liquid scent already packaged in the container 10, as well as, the scent dispenser 12 already being placed in the container 10.

The container 10 serves several purposes. The container 10 is used to transport the liquid scent without any leakage of the liquid scent. The container 10 is used to combine the liquid scent with the absorbent beads 60. The container 10 is used to preserve the inflated absorbent beads 60 in the scent dispenser 12. The liquid scent remains absorbed within the inflated hydrated absorbent beads 60, as long as the container 10 retains an air tight seal using the snap lid 16. Because the liquid scent remains in the absorbent beads 60, there is no liquid scent floating in the container 10, when the proper amount is used. Therefore, a polypropylene jar with an airtight sealing lid acts as a storage container before, during, and after use of the scent dispenser 12. With the scent dispenser system, there is no need for a reservoir to keep feeding what carries the scent. There are no mechanical or movable parts. The absorbent beads 60 hold large volumes of liquid scent. There is no wick is required and no need to refresh the wick when the scent dispenser 12 is stored in the container 10 with the liquid scent. There is also no need for things like the change in barometric pressure to release the liquid scent. The present invention can include some form of heat source in the scent dispenser 12 with the absorbent beads 60. Heat applied to the absorbent beads 60 increases the disbursement of the scent from the absorbent beads 60. Also, there can be other forms of the container, which can be as simple as a sealable plastic bag. The shape of the container 10 and scent dispenser 12 does not have to be cylindrical, but for example could be a rectangular shape.

While different embodiments of the invention have been described in detail herein, it will be appreciated by those skilled in the art that various modifications and alternatives to the embodiments could be developed in light of the overall teachings of the disclosure. Accordingly, the particular arrangements are illustrative only and are not limiting as to the scope of the invention that is to be given the full breadth of any and all equivalents thereof.

I claim:

1. A method of dispensing scent comprising:
   providing absorbent beads which absorb scent containing liquid and can store the scent containing liquid due to hydration of the absorbent beads by the scent containing liquid;
   providing a dispenser having an open volume to contain the absorbent beads and allow expansion of the absorbent beads when the absorbent beads are hydrated and having aeration windows to allow air to pass through the dispenser and over the absorbent beads;
   placing the dispenser with unhydrated absorbent beads in a container with scent containing liquid such that the scent containing liquid contacts the absorbent beads;

allowing the absorbent beads to remain in contact with the scent containing liquid long enough to hydrate the absorbent beads;

removing the dispenser from the container when the absorbent beads are hydrated, wherein the absorbent beads are in the range of 2 mm-5 mm in diameter and further including stacking the absorbent beads in the dispenser such that there is 2 grams of absorbent beads per 0.9 to 1.1 cubic inches of open volume of the dispenser.

* * * * *